United States Patent
Colin et al.

(10) Patent No.: US 8,030,510 B2
(45) Date of Patent: Oct. 4, 2011

(54) PROCESS FOR THE DIRECT SYNTHESIS OF ALKYLHALOSILANES

(75) Inventors: Pascale Colin, Cypres (FR); Cristina Garcia-Escomel, Lyons (FR); Jean-Claude Masteau, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 487 days.

(21) Appl. No.: 11/993,753

(22) PCT Filed: Jun. 7, 2006

(86) PCT No.: PCT/FR2006/001291
§ 371 (c)(1),
(2), (4) Date: Dec. 2, 2008

(87) PCT Pub. No.: WO2006/136673
PCT Pub. Date: Dec. 28, 2006

(65) Prior Publication Data
US 2010/0160664 A1    Jun. 24, 2010

(30) Foreign Application Priority Data

Jun. 22, 2005 (FR) ..................................... 05 06328

(51) Int. Cl.
*C07F 7/00* (2006.01)
(52) U.S. Cl. ....................................... 556/472; 556/463
(58) Field of Classification Search ........................ None
See application file for complete search history.

(56) References Cited

U.S. PATENT DOCUMENTS

| | | | |
|---|---|---|---|
| 2,380,995 A | 8/1945 | Rochow et al. | |
| 2,389,931 A | 11/1945 | Reed et al. | |
| 2,403,370 A | 7/1946 | Hurd et al. | |
| 2,427,605 A | 9/1947 | Hurd et al. | |
| 2,449,821 A | 9/1948 | Sellers et al. | |
| 2,464,033 A | 3/1949 | Gilliam et al. | |
| 4,762,940 A | 8/1988 | Halm et al. | |
| 7,626,050 B2 * | 12/2009 | Colin | ............................. 556/472 |
| 2002/0156310 A1 * | 10/2002 | Inukai et al. | ................... 556/472 |
| 2007/0244337 A1 | 10/2007 | Colin | |

FOREIGN PATENT DOCUMENTS

| | | |
|---|---|---|
| FR | 2861727 | 5/2005 |
| GB | 907 161 | 10/1962 |
| GB | 1 207 466 | 10/1970 |
| SU | 307 650 | 4/2005 |

OTHER PUBLICATIONS

International Search Report for PCT/EP2006/001291 dated Nov. 20, 2006; (4 pages).
Gomez et al., "Determining the Contact Angle of a Nonwetting Liquid in Pores by Liquid Intrusion Calorimetry", Langmuir, 2000, pp. 4374-4379, vol. 16., Centre de Thermodynamique et Microcalorimetrie, France.
Noll, "Chemistry and Technology of Silicones," 1968, pp. 26-41, published by Academic Press Inc., London.
Tamhankar et al., "Autocatalysis in the reduction of cuprous chloride by silicon", Studies in Solid-Solid Reactions, 1981, pp. 1365-1372, vol. 36, Chem. Eng. Sci., Great Britain.
Weber et al., "Research approach to the process of the reaction between silicon and copper chloride powders", Reaction Kinetics, 1988, C.R. Acad. Sci. Paris, vol. 307, Series II, pp. 1155-1161.
Acker et al., "The reactivity in the system CuCI-Si related to the activation of silicon in the Direct Synthesis", Silicon Chemistry, 2003, pp. 195-206, vol. 2, Kluwer Academic Publishers, Netherlands.
Oye et al., "Process Development in the MCS-Production: For Example Watergranulated Silicon Metal", Silicon for the Chemistry Industry, 1994, pp. 55-60, Norway.

* cited by examiner

*Primary Examiner* — Karl J Puttlitz
(74) *Attorney, Agent, or Firm* — Baker Donelson Bearman, Caldwell & Berkowitz, PC

(57) ABSTRACT

Process for preparing alkylhalosilanes are provided. The process involve reacting an alkyl halide with a solid body formed of silicon and a catalytic system.

16 Claims, No Drawings

PROCESS FOR THE DIRECT SYNTHESIS OF ALKYLHALOSILANES

CROSS-REFERENCE TO RELATED APPLICATIONS

The present application is a 371 of application Serial No. PCT/FR2006/001291, filed Jun. 7, 2006, which claims priority to French application no. FR 0506328, filed Jun. 22, 2005.

BACKGROUND OF INVENTION

1. Field of Invention

The present invention relates to improvements relating to the industrial process employed for the direct synthesis of alkylhalosilanes.

2. Description of Related Art

The industrial process for the manufacture of alkylhalosilanes and, for example, of dimethyldichlorosilane, subsequently referred to as DMDCS, is a well known process which is described in particular in the U.S. Pat. No. 2,380,995 and in the work by Walter Noll, Chemistry and Technology of Silicones, 1968, published by Academic Press Inc., London, pages 26-41.

According to this "direct synthesis" or "Rochow synthesis" process, the alkylhalosilanes, for example DMDCS, are manufactured directly by reaction of methyl chloride with a solid contact body formed of silicon and of a catalyst comprising copper, according to the reaction:

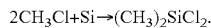
$$2CH_3Cl+Si \rightarrow (CH_3)_2SiCl_2.$$

In reality, other coproducts, such as those mentioned below, are formed during the direct synthesis: other alkylhalosilanes, such as methyltrichlorosilane $CH_3SiCl_3$, subsequently referred to as MTCS, and trimethylchlorosilane $(CH_3)_3SiCl$, subsequently referred to as TMCS; halogenated alkylhydrosilanes, such as, for example, methylhydrodichlorosilane $(CH_3)HSiCl_2$, subsequently referred to as MHDCS; and heavy products which are polysilanes and in particular disilanes, such as, for example, trimethyltrichlorodisilane $(CH_3)_3Si_2Cl_3$ and dimethyltetrachlorodisilane $(CH_3)_2Si_2Cl_4$.

Among all the products obtained by direct synthesis, the dialkyldihalosilane, and for example DMDCS, is the main product, that is to say the product obtained in predominant amount. This product is highly desirable as, after hydrolysis and polymerization, it makes it possible to obtain oils and gums which are base products for the manufacture of silicones.

It is known to use copper, taken in the form of copper metal or in the form of copper-based chemical compounds, as catalyst of the direct synthesis reaction.

It is also known, for the purpose of bringing the performance of the direct synthesis to an economically viable level, to add, to the copper, a promoter combination comprising one or more promoter additive(s); these additives can be: zinc or a zinc halide (U.S. Pat. No. 2,464,033), aluminum (U.S. Pat. Nos. 2,403,370 and 2,427,605), tin, manganese, nickel and silver (British patent GB-A-1 207 466), cobalt (British patent GB-A-907 161), potassium chloride (Soviet patent SU-A-307 650) or arsenic or an arsenic compound (U.S. Pat. No. 4,762,940).

However, despite all the importance of the catalytic systems (copper catalysts as a mixture with a promoter combination) provided in the prior art, research continues in this field in order to obtain better performances than those obtained with the best catalytic systems known previously, in particular the catalytic system comprising copper, zinc and tin.

Various copper sources can be used, mainly, in addition to metallic copper (Cu°), cuprous chloride (CuCl) and oxidized copper.

CuCl is known for contributing a gain in activity or reactivity (evaluated, for example, by weight of the silanes obtained per hour and per kilogram of silicon initially involved) and in selectivity (evaluated, for example, by the percentage by weight of DMDCS formed with respect to the silanes obtained) in comparison with metallic copper. It also makes it possible to reduce the duration of the period of initiation of the reaction and also the amount of the byproducts formed during this initiation period; this is because, in order to carry out the direct synthesis reaction, there is advantageously carried out beforehand, as is well known, an initial stage of activation of the contact body (formed by the combination based on silicon+catalyst+optional promoters); one of the activation means which is highly suitable can consist in bringing said contact body to a certain temperature which can be lower or greater by a few degrees to a few tens of degrees than the temperature chosen for the direct synthesis reaction.

Numerous authors have taken an interest in this initiation period, which corresponds to the reaction between the CuCl and the silicon and which results in the formation of active sites. The mechanism of this reaction is not yet clearly defined after more than fifty years of study. Two reaction models are considered today:

Tamhankar S. S., Gokkarn A. N. and Doraiswamy L. K., 1981, *Chem. Eng. Sci.*, 36, 1365-1372, propose a two-stage mechanism. The first stage is the reduction of the CuCl by the silicon to form metallic copper and $SiCl_4$, followed by the formation of $Cu_3Si$ by diffusion of the copper into the silicon:

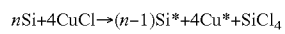
$$nSi+4CuCl \rightarrow (n-1)Si^*+4Cu^*+SiCl_4$$

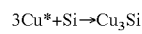
$$3Cu^*+Si \rightarrow Cu_3Si$$

Weber G., Vile D., Souha M. and Guillot B., 1988, *C.R. Acad. Sci. Paris*, Vol. 307, Series II, pages 1155-1161, propose a reaction pathway where the metallic copper is the final product:

$$7Si+12CuCl \rightarrow Cu_3Si+3SiCl_4$$

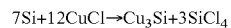
$$31Cu_3Si+12CuCl \rightarrow 7Cu_{15}Si+3SiCl_4$$

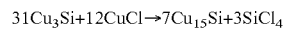
$$9Cu_{15}Si+20CuCl \rightarrow 31Cu_5Si+5SiCl_4$$

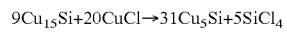
$$Cu_5Si+4CuCl \rightarrow 9Cu+SiCl_4$$

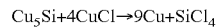

Many factors influence the reaction between Si and CuCl: the concentration of CuCl, the operations of mixing and milling the powders, the thickness of the layer of $SiO_2$ on the silicon, the temperature and the pressure.

Recent studies targeted at determining the initial stage of the reaction between the copper and the CuCl have been published; Acker J., Köhter S., Lewis K. M. and Bohmhammel K., 2003, *Silicon Chemistry*, 2, 195-206. The main conclusion of these studies is that the reaction between the copper chloride and the silicon takes place in the solid state. The slightest change in the surface properties in the CuCl thus results in a modification to the reactivity.

On the basis of these facts, it may be expected that the specific surface of the CuCl used is a key parameter in its reactivity which logically directs us towards the use of fine particles which offer a high surface area for contact with the silicon.

Nevertheless, for reasons of industrial use, the Applicant Company has tested a novel shaping of this product in the form of beads. These spherical beads have a smooth surface and result from an atomization or prilling process. They exhibit the advantage of offering better flow and low dusting in comparison with powders with a low particle size. On the other hand, the Applicant Company expected to obtain mediocre results in terms in particular of reactivity and of selectivity, given their low specific surface and the absence of irregularities on the surface which are known to promote the initiation of solid/solid reactions.

SUMMARY OF INVENTION

It has now been found, surprisingly, and it is this which constitutes the subject matter of the present invention, that:
- if the copper catalyst used to carry out the direct synthesis reaction is involved in the form of cuprous halide beads,
- it is then observed that said beads result in the use of the CuCl being facilitated industrially by bringing about the disappearance of the constraints related to poor flow in pneumatic conveying and to dusting during handling, without loss in reactivity or in selectivity of the direct synthesis reaction.

The present invention consequently provides a process for the preparation of alkylhalosilanes by reaction of an alkyl halide, preferably $CH_3Cl$, with a solid body, referred to as contact body, formed of silicon and of a catalytic system comprising ($\alpha$) a copper catalyst and ($\beta$) a group of promoter additives comprising:
- an additive $\beta1$ chosen from metallic zinc, a zinc-based compound and a mixture of these entities,
- an additive $\beta2$ chosen from tin, a tin-based compound and a mixture of these entities,
- optionally an additive $\beta3$ chosen from cesium, potassium, rubidium, phosphorus, a compound derived from these metals/semimetals and a mixture of these entities, said direct synthesis process being characterized in that the copper catalyst (a) is in the form of cuprous halide beads, said beads exhibiting the following specifications:
- a sphericity factor which lies within the range from 0.6 to 1;
- a particle size distribution where the value of $D_{50}$ lies within the range from 50 to 1500 μm; it is difficult technically to fall, by the atomization process which will be discussed below, below the limit 50; above the limit 1500, reactivity is lost;
- a porous texture which is equal to or less than 0.2 ml/g for a pore diameter ranging from 0.1 to 10 μm; the lower limit can be as small as that equal to zero;
- and a flowability which is equal to or greater than 8; with regard to the upper limit, a person skilled in the art knows that it can be as high as an infinite value when the cohesive force (as defined below) tends towards zero.

I—Measurements and Tests Used:
A) Sphericity Factor

DETAILED DESCRIPTION OF PREFERRED A EMBODIMENT

The objects produced by atomization, spray drying, spray cooling or prilling exhibit a spherical shape. The following procedure by image analysis is used to quantify the sphericity of the objects. The characteristic lengths of the small and large diameters are measured for each object on a minimum of 100 objects. For each object, the sphericity factor is defined as the ratio of the small diameter to the large diameter. For a perfect sphere, the ratio is 1. For grains of variable morphology, this ratio is less than 1 and tends towards 1 when perfect sphericity is approached.

This sphericity factor is calculated according to the ratio of the diameters for 100 objects withdrawn and the mean of the sphericity factors is taken. To do this, in a way known per se, the sample of the particles is dispersed over a glass plate placed under an optical microscope connected to an image analysis system. It is also possible to use the procedure described in the work: "Silicon for the Chemical Industry", II, Loen, Norway, 8-10 Jun. 1994, by Oye H. A., Rong H. M., Nygaard L., Schüssler G. and Tusset J. Kr., Tapir Vorlag Trondheim.

B) Particle Size Distribution:

The particle size distribution of the objects is obtained by measurement by laser diffraction on a Malvern particle sizer using the Sirocco dry route module (pressure condition: 3 bar). The quantities used in this document relate to $D_{10}$ (10% of particles by weight exhibit a diameter of less than $D_{10}$ in μm), $D_{50}$ (50% of particles by weight exhibit a diameter of less than $D_{50}$ in μm) and $D_{90}$ (90% of particles by weight exhibit a diameter of less than $D_{90}$ in μm). The coefficient of variation quantifying the size of the distribution will be defined such that:

$$CV = \frac{(D_{90} - D_{10})}{2 \times D_{50}}$$

The particle size analysis by laser diffraction is carried out according to the instructions of the standard AFNOR NF ISO 13320-1.

C) Porous Texture:

The porous texture of the objects is determined by mercury porosimetry using an Autopore IV device from Micromeritics. It is a method based on the intrusion of mercury into the pore network (intergranular or intragranular). This intrusion is managed via a rise in pressure. The pressure (P) range used is from 0.003 MPa to 400 MPa. The diameter of the pores (2r) is easily related to the pressure applied via Washburn's equation:

$$r = (-)\frac{2 \cdot \gamma_{LV} \cdot \cos\theta}{P}$$

The parameters taken into account for the mercury are respectively: $485 \times 10^{-5}$ N/cm for the surface tension $\gamma_{LV}$ and 130° for the value of the wetting angle $\theta$. The results are presented as a volume of mercury introduced per gram of sample as a function of the pressure (thus of the diameter of the pores) applied.

Mercury porosimetry is a technical concept which is well known to a person skilled in the art; for further details, reference may in particular be made to the paper: Gomez F., Denoyel R. and Rouquerol J., *Langmuir*, 16, 3474 (2000).

D) Flowability:

The flowability of the powder is measured by shearing a sample with an annular cell (sold by D. Schulze, Germany). The preshearing of the powder is carried out on a cell with a surface area of 81 cm² with a normal stress equivalent to a weight of 4.3 kg. The shear points for plotting the yield locus of the sample are obtained for 4 stresses below the stress of the preshearing (typically for stresses equivalent by weight to 0.4, 0.7, 1.7 and 2.5 kg). From the Mohr circles (in a diagram of shear stress as a function of the normal stresses), 2 stresses are obtained on the yield locus (one is the end of the large Mohr circle which passes through the preshear point and is referred to as normal stress in the main direction and the other is the end of the small Mohr circle, circle tangent to the yield locus and passing through the origin, which will be referred to as cohesive force). The ratio of normal stress in the main direction to the cohesive force is a dimensionless number, the flowability index. From the Jenike scale, it is possible to classify the flowability of powders as a function of the values of the index:

i<2 Highly cohesive product which does not flow
2<i<4 Cohesive product
4<i<10 Product which flows easily
i>10 Product which flows freely or free-flowing product The flowability of powders is a technical concept which is also well known to a person skilled in the art; for further details, reference may in particular be made to the work: "Standard shear testing technique for particulate solids using the Jenike shear cell", published by "The Institution of Chemical Engineers", 1989 (ISBN: 0 85295 232 5).

II—Conditions for Implementing the Invention with Regard to the Copper Catalyst ($\alpha$):

In accordance with a preferred embodiment of the invention, the copper catalyst ($\alpha$) is in the form of cuprous halide beads, said beads exhibiting the following specifications:
  a sphericity factor which lies within the range from 0.8 to 1;
  a particle size distribution where the value of $D_{50}$ lies within the range from 50 to 800 µm;
  a porous texture which is equal to or less than 0.1 ml/g for a pore diameter ranging from 0.1 to 10 µm;
  and a flowability which is equal to or greater than 10.

In accordance with a more preferred embodiment of the invention, the copper catalyst ($\alpha$) is in the form of cuprous halide beads, said beads exhibiting the following specifications:
  a sphericity factor which lies within the range from 0.9 to 1;
  a particle size distribution where the value of $D_{50}$ lies within the range from 50 to 500 µm;
  a porous texture which is equal to or less than 0.05 ml/g for a pore diameter ranging from 0.1 to 10 µm;
  and a flowability which is equal to or greater than 12.

The copper catalyst (a) is generally used at a content by weight ranging from 1 to 20%, preferably between 2 to 12%, with respect to the weight of silicon involved.

III—Other Conditions for Implementing the Invention:

According to the embodiment defined above, the catalytic system additionally comprises a promoter additive $\beta1$ based on metallic zinc and/or a zinc compound; use is preferably made of metallic zinc and/or zinc chloride.

The promoter additive $\beta1$ is present at a content by weight lying within the range from 0.01 to 2%, preferably from 0.02 to 0.5% (calculated as zinc metal with respect to the weight of silicon involved). Up to 90% by weight of the zinc, preferably up to 50% by weight of the zinc, can be replaced by another metal which catalyzes the chloridation of copper and/or which forms a eutectic or a phase with a low melting point with copper salts and/or alkali metal salts. Mention may be made, as metal which may be suitable, of cadmium, aluminum, manganese, nickel and silver.

The content by weight of tin and/or of tin compound (promoter additive $\beta2$, the content of which is calculated as weight of tin metal) lies within the range from 10 to 500 ppm and preferably from 30 to 300 ppm, with respect to the weight of silicon involved.

It is necessary to have at least 10 ppm of tin metal.

In addition, a content by weight of greater than 500 ppm would have a harmful effect on the reaction and in particular on the selectivity. Use is made, as tin-based compound, for example, of tin chloride. The promoter additive $\beta2$ which is preferably used is tin metal; advantageously, this metallic tin can be added in the form of bronze.

With regard to the optional promoter additive $\beta3$, in the case where one of them is used, the following points will be specified below:
  the content by weight of promoter additive $\beta3$ of metal type (calculated as weight of alkali metal, with respect to the weight of silicon involved) lies within the range from 0.01 to 2% by weight and preferably from 0.05 to 1.0% by weight; below 0.01% by weight, the action of the alkali metal is not really detectable and, above 2% by weight, the alkali metal does not have the expected effect on the selectivity;
  use may be made, as compound of an alkali metal chosen from Cs, K and Rb, of: halides and for example the chloride; carboxylates and for example the formate or the acetate; cesium chloride, potassium chloride, rubidium chloride and/or a mixture of these compounds are the promoter additives $\beta3$ of metal type which are preferably used;
  when the promoter additive $\beta3$ is of semimetal type, its content by weight (calculated as weight of elemental phosphorus, with respect to the weight of silicon involved) lies within the range from 50 to 3000 ppm and preferably from 80 to 1500 ppm and more preferably still from 90 to 800 ppm; below 50 ppm, the action of the phosphorus is not really detectable and, above 3000 ppm, the phosphorus has a poisonous effect which reduces the productive output;
  the phosphorus which is used as promoter additive can be elemental phosphorus, such as, for example, red phosphorus, white phosphorus and black phosphorus. Use may be made, as phosphorus-based compound, of: metal phosphides, and for example aluminum phosphide, calcium phosphide $Ca_3P_2$, copper phosphide $Cu_3P$, nickel phosphide $NiP_2$, tin phosphide SnP, the iron phosphides FeP, $Fe_2P$ and $Fe_3P$, the zinc phosphides $Zn_3P_2$ and $ZnP_2$, or silicon phosphide; or phosphorus-based compounds capable of forming metal phosphides of the type of those mentioned above during the direct synthesis reaction between the alkyl halide and the contact body based on silicon and on the catalytic system ($\alpha$)+($\beta$). Use may also be made, as other phosphorus-based compounds, of certain alloys which are known to comprise both phosphorus and a metal part and which are readily available commercially, for example the copper-phosphorus alloys which comprise approximately from 5 to 15% by weight of phosphorus. Copper phosphide $Cu_3P$, the copper-phosphorus alloys and/or a mixture of these compounds are the promoter additives $\beta3$ of semimetal type which are preferably used.

To summarize, the additive $\beta3$ which is preferably used is cesium chloride, potassium chloride, rubidium chloride, copper phosphide $Cu_3P$, a copper-phosphorus alloy and/or a mixture of these compounds.

As for the rest, it is desirable for the particle size of the silicon to be such that the mean diameter of at least 50% by weight of the particles is between 10 and 500 µm and preferably between 60 and 200 µm. The group of promoters ($\beta$) is also found in the form of particles, the mean diameter of at least 50% by weight of the particles advantageously being between 1 and 100 µm.

The direct synthesis process according to the invention can generally be carried out in one of the three following types of apparatus: a reactor of the stirred bed type, such as that described in the U.S. Pat. No. 2,449,821, a reactor of the fluidized bed type, such as that described in the U.S. Pat. No. 2,389,931, or a rotary kiln.

The direct synthesis reaction takes place at a temperature lying within the range from 260 to 400° C. and preferably from 280 to 380° C. It can be carried out, in all or part, under an absolute pressure of alkyl halide equal to atmospheric pressure ($10^5$ Pa) or greater than atmospheric pressure; when the latter case prevails, the reaction is generally carried out under an absolute pressure ranging from $1.1 \times 10^5$ Pa to $8 \times 10^5$ Pa and preferably ranging from $1.5 \times 10^5$ Pa to $4 \times 10^5$ Pa.

In order to carry out the direct synthesis reaction, an initial stage of activation of the contact body (formed by the combination based on silicon+catalyst+promoters) is advantageously performed beforehand, as is well known; one of the activation means which is highly suitable can consist in bringing said contact body to a certain temperature which can be lower or greater by a few degrees to several tens of degrees than the temperature chosen for the direct synthesis reaction and which lies within the general or preferred range mentioned above.

On using the catalytic system $(\alpha)+(\beta)$ according to the invention, it is possible to obtain, when the reaction is carried out, both in a stirred bed and in a fluidized bed, at a temperature ranging from 260° C. to 400° C. and preferably ranging from 280 to 380° C., a very satisfactory high mean activity and a high selectivity for dialkyldihalosilane; more specifically:
- as regards the mean activity of the catalytic system, it is, for example, of the order of or greater than 210 g of silanes/h/kg,
- as regards the selectivity, evaluated, for example, by the percentage by weight of DMDCS formed with respect to the silanes obtained: the value obtained is generally greater than 85% by weight.

Other advantages and characteristics of the present invention will become apparent on reading the following examples, given by way of illustration but without implied limitation.

In the following examples, unless otherwise mentioned, use is made of a cylindrical pilot-scale reactor with an internal diameter of 60 mm and a height of 250 mm equipped at its base with a sparger made of sintered glass. The silicon is charged in the form of a powder, the mean size of at least 50% by weight of the particles of which is between 60 and 200 μm.

The reaction is carried out in a stirred bed and the reactor is equipped with an external heating element.

The present invention will be better understood in the light of the following examples.

EXAMPLES

In these examples, the characteristics of the CuCl employed are listed in the following table 1:

TABLE 1

| Product | CuCl A | CuCl B | CuCl C |
|---|---|---|---|
| Source | Laboratory grade | Goldschmidt | Goldschmidt |
| Sphericity factor | Inapplicable as product acicular | 0.92 | 0.92 |
| $D_{10}$ (μm) | 5 | 74 | 15 |
| $D_{50}$ (μm) | 19 | 250 | 95 |

TABLE 1-continued

| Product | CuCl A | CuCl B | CuCl C |
|---|---|---|---|
| $D_{90}$ (μm) | 45 | 590 | 283 |
| CV | 1.05 | 1.03 | 1.41 |
| Volume of intrusion of mercury over the range (0.1-10 μm) (ml/g) | 0.010 | 0.015 | 0.010 |
| Flowability | 2.5 | 23 | 22 |

Comparative Test A:

Catalytic System: CuCl A/$ZnCl_2$/Sn

A powder composed of 210 g of silicon, 16.5 g of CuCl A, 1.44 g of $ZnCl_2$ and 0.38 g of bronze comprising 10% by weight of tin is charged to a cylindrical vertical glass reactor equipped with a metal stirrer and with a sparger made of sintered glass. The reactor is gradually heated to 200° C. under a stream of nitrogen. Then, while continuing to raise the temperature of the reactor, the nitrogen tap is closed and the introduction is begun of methyl chloride with a flow rate, measured at 20° C., of 60 g/h. The temperature of the reactor is regulated at 300° C. and the methyl chloride flow rate is maintained at 60 g/h for 8 hours; the test takes place at atmospheric pressure.

The mixture produced is analyzed by gas chromatography and it is characterized by a proportion of DMDCS equal to 86.5% (% by weight).

The mean productive output of the test is equal to 193 g of MCS/kg of Si involved/h.

Example 1

Catalytic System: CuCl B/$ZnCl_2$/Sn

A powder composed of 210 g of silicon, 16.5 g of CuCl A, 1.44 g of $ZnCl_2$ and 0.38 g of bronze comprising 10% by weight of tin is charged to a cylindrical vertical glass reactor equipped with a metal stirrer and with a sparger made of sintered glass. The reactor is gradually heated to 200° C. under a stream of nitrogen. Then, while continuing to raise the temperature of the reactor, the nitrogen tap is closed and the introduction is begun of methyl chloride with a flow rate, measured at 20° C., of 60 g/h. The temperature of the reactor is regulated at 300° C. and the methyl chloride flow rate is maintained at 60 g/h for 8 hours; the test takes place at atmospheric pressure.

The mixture produced is analyzed by gas chromatography and it is characterized by a proportion of DMDCS equal to 88.2% (% by weight).

The mean productive output of the test is equal to 209 g of MCS/kg of Si involved/h.

Example 2

Catalytic System: CuCl C/$ZnCl_2$/Sn

A powder composed of 210 g of silicon, 16.5 g of CuCl A, 1.44 g of $ZnCl_2$ and 0.38 g of bronze comprising 10% by weight of tin is charged to a cylindrical vertical glass reactor equipped with a metal stirrer and with a sparger made of sintered glass. The reactor is gradually heated to 200° C. under a stream of nitrogen. Then, while continuing to raise the temperature of the reactor, the nitrogen tap is closed and the introduction is begun of methyl chloride with a flow rate, measured at 20° C., of 60 g/h. The temperature of the reactor is regulated at 300° C. and the methyl chloride flow rate is maintained at 60 g/h for 8 hours; the test takes place at atmospheric pressure.

The mixture produced is analyzed by gas chromatography and it is characterized by a proportion of DMDCS equal to 87.6% (% by weight).

The mean productive output of the test is equal to 213 g of MCS/kg of Si involved/h.

What is claimed is:

1. A process for the preparation of alkylhalosilanes comprising reacting an alkyl halide with a solid body, formed of silicon and of a catalytic system comprising (α) a copper catalyst and (β) a group of promoter additives comprising:
    at least one additive β1 selected from the group consisting of metallic zinc, and a zinc-based compound,
    at least one additive β2 selected from the group consisting of tin, and a tin-based compound,
    optionally at least one additive β3 selected from the group consisting of: halides carboxylates, formates, and acetates of cesium, potassium, and rubidium; phosphorus; metal phosphides; calcium phosphide; silicon phosphide; phosphorous-based compounds capable of forming metal phosphides; copper-phosphorous alloys; copper phosphide; and mixtures thereof,
    wherein the copper catalyst (α) is in the form of cuprous halide beads, said beads exhibiting the following specifications:
    (i) a sphericity factor which lies within the range from 0.6 to 1;
    (ii) a particle size distribution where the value of $D_{50}$ lies within the range from 50 to 1500 μm;
    (iii) a porous texture which is equal to or less than 0.2 ml/g for a pore diameter ranging from 0.1 to 10 μm; and
    (iv) a flowability which is equal to or greater than 8.

2. The process as claimed in claim 1, wherein the catalyst (α) is in the form of cuprous halide beads, said beads exhibiting the following specifications:
    (i) a sphericity factor which lies within the range from 0.8 to 1;
    (ii) a particle size distribution where the value of $D_{50}$ lies within the range from 50 to 800 μm;
    (iii) a porous texture which is equal to or less than 0.1 ml/g for a pore diameter ranging from 0.1 to 10 μm; and
    (iv) a flowability which is equal to or greater than 10.

3. The process as claimed in claim 1, wherein the catalyst (α) is in the form of cuprous halide beads, said beads exhibiting the following specifications:
    (i) a sphericity factor which lies within the range from 0.9 to 1;
    (ii) a particle size distribution where the value of $D_{50}$ lies within the range from 50 to 500 μm;
    (iii) a porous texture which is equal to or less than 0.05 ml/g for a pore diameter ranging from 0.1 to 10 μm; and
    (iv) a flowability which is equal to or greater than 12.

4. The process as claimed in claim 1 wherein the part (α) of the catalytic system is used at a content by weight of 1 to 20%, with respect to the total weight of silicon involved.

5. The process as claimed in claim 1, wherein the content of additive β1 lies within the range from 0.01 to 2.0%.

6. The process as claimed in claim 1, wherein the additive β1 is metallic zinc and/or zinc chloride.

7. The process as claimed in claim 1, wherein the content of additive β2 lies within the range from 10 to 500 ppm.

8. The process as claimed in claim 1, wherein the additive β2 is tin metal.

9. The process as claimed in claim 8, wherein the metallic tin is involved in the form of bronze.

10. The process as claimed in claim 1, wherein the content of additive β3 lies within the range from: 0.01 to 2.0%, when an additive β3 based on alkali metal is used, and from 50 to 3000 ppm, in the case of the use of an additive β3 based on semimetal.

11. The process as claimed in claim 1, wherein the additive β3 is at least one of cesium chloride, potassium chloride, rubidium chloride, copper phosphide $Cu_3P$, and/or a copper-phosphorus alloy.

12. The process as claimed in claim 1, wherein said process comprises a direct synthesis reaction that is carried out at a temperature lying within the range from 260° C. to 400° C.

13. The process of claim 1, wherein said catalyst (α) is produced by a process selected from the group consisting of atomization, spray drying, spray cooling, and prilling.

14. The process of claim 1, wherein said silicon has a particle size distribution such that the mean diameter of at least 50% by weight of said silicon is between 10 and 500 μm.

15. The process of claim 1, wherein said additives β have a particle size distribution such that the mean diameter of at least 50% by weight of said additives β is between 1 and 100 μm.

16. The process of claim 1, wherein said process is performed at greater than atmospheric pressure.

* * * * *